US00PP08307P

United States Patent [19]

Schumann

[11] Patent Number: Plant 8,307

[45] Date of Patent: Jul. 13, 1993

[54] GERANIUM PLANT NAMED FISRINA

[75] Inventor: Ingeborg Schumann, Münster, Fed. Rep. of Germany

[73] Assignee: Florfis AG, Binningen, Switzerland

[21] Appl. No.: 779,297

[22] Filed: Oct. 18, 1991

[51] Int. Cl.[5] ..... A01H 5/00
[52] U.S. Cl. ..... Plt./87.12
[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fisrina, particularly characterized by the combined features of rose red semi-double flowers, medium green leaves with narrow zonation, vigorous growth in combination with comparatively short internodes, good branching characteristics, rich flower production and good heat resistance.

1 Drawing Sheet

The present invention comprises a new and distinct cultivar of geranium, botanically known as *Pelargonium peltatum L'Hert*, and hereinafter referred to by the cultivar name Fisrina.

Fisrina is a product of planned breeding program which had the objective of creating new ivy geranium cultivars with red flower color, semi-double flower form, good branching and rich flowering.

Fisrina was originated from a hybridization made by the inventor Ingeborg Schumann in a controlled breeding program in Galdar, Gran Canaria, Spain in 1985. Fisrina is the result of a selfing of an unnamed hybrid seedling derived from a cross between the female parent, identified as No. 418 from the Leuenberger Collection and having red semi-double flowers, vigorous growth, and strong zonation, and the male parent Pelenberger, characterized by rose red single flowers with narrow petals, vigorous growth, and foliage without zonation.

Fisrina was discovered and selected as one flowering plant within the progeny of the stated cross by Ingeborg Schumann in spring 1986 in a controlled environment in Galdar, Gran Canaria, Spain.

The first act of asexual reproduction of Fisrina was accomplished when vegetative cuttings were taken from the initial selection in February 1987 in a controlled environment in Hillscheid, Federal Republic of Germany by, or under the supervision of, Ingebor Schumann.

Horticultural examination of rooted cuttings initiated in May 1987 and continuing thereafter has demonstrated that the combination of characteristics as herein disclosed for Fisrina are firmly fixed and are retained through successive generations of asexual reproduction.

Fisrina has not been observed under all possible environmental conditions. The phenotype may vary somewhat with variations in environment such as temperature, light intensity and day length, without, however, any variance in the genotype. The following observations measurements, and comparisons describe plants grown in Hillscheid, Federal Republic of Germany under greenhouse conditions which approximate those generally used in commercial practice.

The following traits have been repeatedly observed and are determined to be basic characteristics of Fisrina, which in combination distinguish this geranium as a new and distinct cultivar:

1. Semi-double flowers rose red in color

2. Weak purple veins on upper petals
3. Medium to late flower response
4. Medium green foliage
5. Comparatively small leaves with narrow zonation
6. Vigorous growth
7. Well branched, bushy plant habit
8. Prolific flower production
9. Good heat resistance Of the many commercial cultivars known to the present inventor, the most similar in comparison to Fisrina is Rigi. Reference is made to attached Chart A which compares certain characteristics of Fisrina to those same characteristics of Rigi. In general comparison to Rigi, Fisrina has a more reddish shade of flower color, more but slightly smaller leaves smaller flowers and umbels, but much higher flower production and more vigorous growth. Purple markings on petals as well as zonation on leaves are somewhat weaker in Fisrina than in Rigi.

The accompanying color photographic drawing in a side elevational view showing typical flower and foliage characteristics of a comparatively young Fisrina, with colors being as true as possible with illustrations of this type.

In the following description color references are made to the Royal Horticultural Society Color Chart. The color values were determined indoors from flowers taken from plants grown outdoors in June at Hillscheid, Federal Republic of Germany.

Classification:

*Botanical.*—A hybrid of the species *Pelargonium peltatum L'Hert.*

*Commercial.*—Ivy geranium, cv. Fisrina.

INFLORESCENCE

A. Umbel:

*Average diameter.*—97 mm.
*Average depth.*—55 mm.
*Peduncle length.*—120 mm.
*Pedicel length.*—27 mm.
*Pedicel color.*—Green, no anthocyanin.
*Number of flowers per umbel.*—7.3.

B. Corolla:

*Average diameter.*—50 mm.
*Form.*—Semi-double.
*Number of Petals.*—10–14.

*Color (general tonality from a distance of three meters).*—Rose red.

*Color of upper surface of petals (when stamens are mature).*—R.H.S. main color between 52A and 57A with slight fading on maturity; there is weak marking consisting of two darker red veins on the surface.

*Color of lower surface of petals.*—R.H.S. 57B-C.

*Color of lower surface.*—R.H.S. between 52C and 57C with slight fading on maturity.

*Sepals.*—Green, no anthocyanin.

*Petaloids.*—There is average of two or three small petals with a stamen on top; petaloids are essentially transformed anthers.

C. Bud:

*Shape.*—Elongated.

*Color (sepals).*—Light green.

*Color (tips of petals).*—Red.

D. Reproductive organs:

*Androecium.*—6–8 anthers, most of these fertile with orange-yellow pollen.

*Gynoecium.*—5–6 lobed stigma, pink.

E. Spring flowering response period: In Hillscheid, Federal Republic of Germany, in 1989 45% of plants with at least 1 flower opened 11 weeks after planting of unrooted cuttings.

F. Outdoor flower production: The flower count in 1989 in Hillscheid, Federal Republic of Germany indicated between 210 and 220 flowers per plant for May through September observation period.

G. Durability: Good heat resistance, Good rain resistance.

H. Seed production: Fisrina is fertile and produces seed after pollination, but sets only a few seeds spontaneously.

PLANT

A. Foliage:

*Form.*—Ivy shaped.

*Margin.*—Entire.

*Color (upper surface).*—Medium green, approximately R.H.S. 137C-D.

*Color (zonation).*—Brown narrow ring-shaped zonation, approximately R.H.S. 166A.

*Tolerance of botrytis.*—Medium to good.

*Size.*—Normal to slightly smaller relative to average size for this species.

B. General appearance and form:

*Internode length.*—3.0–4.5 cm.

*Branching pattern.*—7.0 branches per plant (after 12 weeks) self-pinching.

*Length of branches.*—80 cm in August.

CHART A

| | FISRINA | RIGI |
|---|---|---|
| Flower color | rose red between 52A and 57B | pink 57C |
| Diameter of umbel | 9–9.5 cm | 10.5–11.5 |
| Plant habit | bushy | loose |
| Branching habit (number of branches per plant | 7.0 | 4.2 |
| Beginning of flowering (Percent of flowering plants after 11 weeks | 45% | 75% |
| Number of umbels | 215 | 71 |

I claim:

1. A new and distinct cultivar of geranium plant named Fisrina, as illustrated and described.

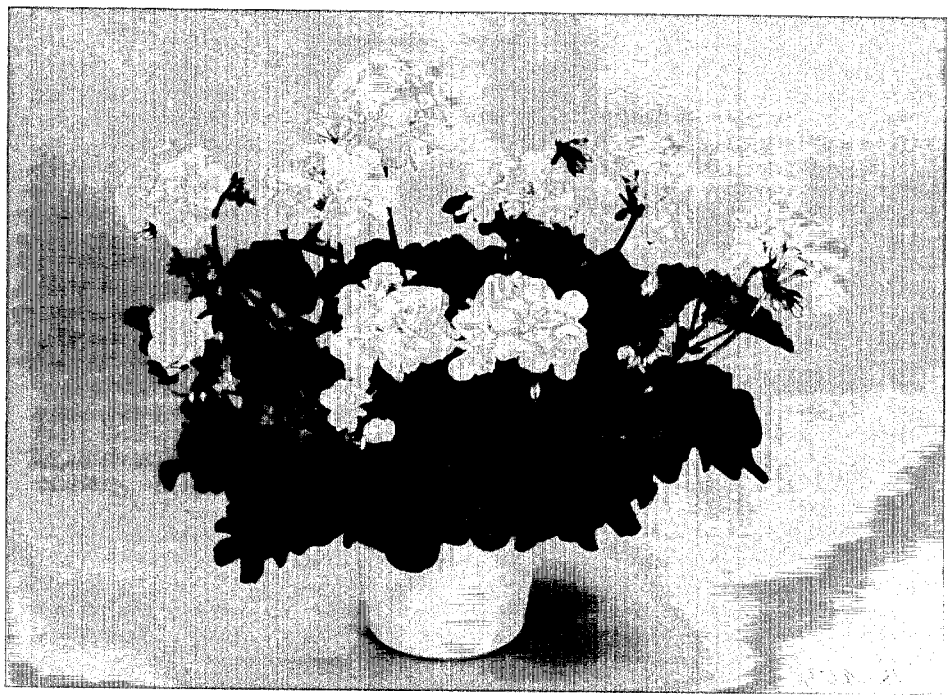

* * * * *